(12) United States Patent
Pivonka (10) Patent No.: US 9,377,788 B2
(45) Date of Patent: *Jun. 28, 2016

(54) APPARATUS FOR FLAMER FUEL PRESSURE CONTROL

(71) Applicant: Flame Engineering, Inc., Lacrosse, KS (US)

(72) Inventor: Ralph M. Pivonka, Lacrosse, KS (US)

(73) Assignee: Flame Engineering, Inc., Lacrosse, KS (US)

(*) Notice: Subject to any disclaimer, the term of this patent is extended or adjusted under 35 U.S.C. 154(b) by 276 days.

This patent is subject to a terminal disclaimer.

(21) Appl. No.: 14/093,838

(22) Filed: Dec. 2, 2013

(65) Prior Publication Data

US 2014/0083527 A1 Mar. 27, 2014

Related U.S. Application Data

(60) Division of application No. 12/835,109, filed on Jul. 13, 2010, now Pat. No. 8,623,277, and a division of application No. 11/421,133, filed on May 31, 2006, now Pat. No. 7,833,476, and a continuation-in-part of application No. 10/687,854, filed on Oct. 17, 2003, now Pat. No. 7,470,395.

(51) Int. Cl.
*F25B 19/00* (2006.01)
*G05D 16/20* (2006.01)
(Continued)

(52) U.S. Cl.
CPC ............... *G05D 16/20* (2013.01); *A01M 15/00* (2013.01); *A01M 21/04* (2013.01); *A61L 2/04* (2013.01); *Y10T 137/7761* (2015.04);
(Continued)

(58) Field of Classification Search
CPC .............................. G05D 16/20; F23B 19/00
USPC ........... 422/18, 1; 137/487.5; 62/48.1, 50.2, 7
See application file for complete search history.

(56) References Cited

U.S. PATENT DOCUMENTS

| 3,425,407 A | 2/1969 | Furman et al. |
| 3,962,044 A | 6/1976 | Mackenzie |

(Continued)

FOREIGN PATENT DOCUMENTS

| GB | 1567505 | 5/1980 |
| JP | 06078658 | 3/1994 |
| JP | 1075704 | 3/1998 |

OTHER PUBLICATIONS

3 pages of an Executive Summary entitled LP-Gas for Weed and Nematode Control in Agricultural dated Oct. 2001—by Wayne A. LePori—printed from the website displayed at the bottom of the page.

*Primary Examiner* — Gregory Huson
*Assistant Examiner* — Nikhil Mashruwala
(74) *Attorney, Agent, or Firm* — Sturm & Fix LLP (57) ABSTRACT

A flamer may be used to sterilize poultry litter, soil, concrete, etc. The stationary or mobile flamer disclosed comprises a hood to contain the heat, an external frame, and burners. A fuel tank may be carried on the flamer or on a tractor. An additional embodiment provides for mounting the flamer on wheels, permitting the unit to be towed by a truck, four-wheeler, tractor, etc. The burners are adjustable as to angle, and fueling rate. A pressure in the fuel system is controlled by selectively switching between the liquid and vaporous components of the fuel. By limiting how low the pressure may fall, the flow of fuel from the tank to the torches is more consistent.

3 Claims, 12 Drawing Sheets

(51) Int. Cl.
*A01M 15/00* (2006.01)
*A01M 21/04* (2006.01)
*A61L 2/04* (2006.01)

(52) U.S. Cl.
CPC ..... *Y10T 137/7835* (2015.04); *Y10T 137/7836* (2015.04); *Y10T 137/86397* (2015.04)

(56) References Cited

U.S. PATENT DOCUMENTS

| | | | |
|---|---|---|---|
| 4,088,122 A | 5/1978 | Miles | |
| 4,250,869 A | 2/1981 | Doyle | |
| 4,404,984 A | 9/1983 | Jones | |
| 4,406,129 A * | 9/1983 | Mills | B60K 15/013 137/539.5 |
| 4,420,901 A | 12/1983 | Clarke | |
| 4,805,927 A | 2/1989 | Stephenson | |
| 5,030,086 A | 7/1991 | Jones | |
| 5,826,371 A | 10/1998 | Benjamin | |
| 6,014,835 A | 1/2000 | Pivonka | |
| 6,240,982 B1 | 6/2001 | Bonne | |
| 6,517,342 B2 | 2/2003 | Van der Veen | |
| 6,913,004 B2 | 7/2005 | Pellizzari | |
| 7,406,871 B2 * | 8/2008 | Sugiura | F02D 1/0025 123/198 D |
| 7,690,208 B2 | 4/2010 | Immel | |
| 2003/0192485 A1 | 10/2003 | Opfel | |
| 2012/0060935 A1 | 3/2012 | Carter | |
| 2015/0252947 A1 * | 9/2015 | Snyder | F17C 7/02 62/50.2 |

* cited by examiner

APPARATUS FOR FLAMER FUEL PRESSURE CONTROL

CROSS REFERENCE TO RELATED APPLICATIONS

This application is a divisional of U.S. Ser. No. 12/835,109 filed Jul. 13, 2010 which is a divisional of U.S. Ser. No. 11/421,133 filed May 31, 2006, now U.S. Pat. No. 7,833,476, issued Nov. 16, 2010, which is a continuation-in-part application of U.S. patent application Ser. No. 10/687,854, filed Oct. 17, 2003, now U.S. Pat. No. 7,470,395, issued Dec. 30, 2008, all of which are incorporated herein by reference in their entirety.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates generally to a flamer. More particularly the present invention relates to a fuel supply pressure controller for a stationary or mobile flamer.

2. Background Art

Poultry litter may be sterilized by chemical means. As usual, the issue becomes that of chemical retention and the effect of the chemicals on the environment. Poultry litter may also be sterilized by flame heat, as disclosed by Mackenzie in U.S. Pat. No. 3,962,044. Because he discloses stationary equipment for litter sterilization, the method of Mackenzie '044 requires a significant investment in machinery to handle the litter for sterilization. Space for the machinery and appropriate shelter is also necessary.

A tractor drawn flamer was disclosed by Pivonka in U.S. Pat. No. 6,014,835 for the purpose of flame cultivation. Because of its open-flame design, the flamer of Pivonka '835 is not suitable for sterilization purposes. Because the use of the Pivonka '835 flamer for sterilization was not considered, there was no motivation to make the flamer enclosed for sterilization.

Handheld torches and flamers are available, again especially for weed control and ice melting. These flamers are not suitable for the large task of sterilizing large amounts of poultry litter or soil, etc. due to their small coverage and the weight that must be supported or drawn by the user.

Propane, commonly called Liquified Petrolium (LP), is usually the fuel used for flamers such as those used to sterilize poultry litter. The equilibrium pressure inside a propane tank containing a saturated mixture of liquid and vaporous propane is strictly a function of the temperature of these contents. However, during periods of heavy fuel usage, the pressure inside the tank may fluctuate due to finite times required for boiling off of the liquid into vapor and variations in temperature.

The rate flow of the fuel for a flamer is a function of the tank pressure. When the tank pressure varies, the fuel flow rate varies as well. Flaming, then, regardless of the purpose, may suffer in quality as long as the tank pressure is permitted to vary.

A tractor drawn flamer was disclosed by Pivonka in U.S. Pat. No. 6,014,835, which is hereby incorporated by reference. This tractor drawn flamer is used for flame cultivation.

A tractor drawn or mounted flamer was disclosed by Pivonka in U.S. patent application 2005/0084409 (Ser. No. 10/687,854), which is hereby incorporated by reference. This tractor drawn flamer is used for flame sterilization of poultry litter.

Neither of the above mobile flamers make use of a pressure control system.

There is therefore a need for a fuel pressure control system to use in conjunction with stationary and mobile flamers.

BRIEF SUMMARY OF THE INVENTION

An object of the present invention is to provide control of the fuel supply pressure for a flamer. Such stationary and mobile flamers may be used, for instance, to sterilize materials such as poultry litter, soil, and pavement; or for weed eradication, or softening asphalt. Tractors are ubiquitous in the agricultural industry. Because of tractors' versatility, implements are often made to mount to a tractor or be drawn behind a tractor. Heat has long been used for sterilization. So is it possible to utilize a tractor for transporting a mobile flamer to provide heat for sterilization. Such a flamer is mounted on the tractor—preferably on a three-point hitch or quick coupler. An additional embodiment of the present invention is represented by a flamer on wheels or skids and drawn behind a vehicle as a trailer.

The fuel supply pressure control system of the present invention provides a way to keep the fuel tank pressure near a predetermined value even during heavy fuel usage. To effect this control, fuel feed is selected from the vaporous and liquid components of the fuel. When vapor is being drawn from the tank, an equal amount of liquid must boil off to replace the vapor removed, plus a small volume equal to the volume of liquid converted to vapor. In contrast, when liquid is drawn off the fuel tank, the volume of liquid is much smaller than the volume of the same mass of liquid, i.e. the volume of the liquid is much smaller that the volume of the vapor. So the volume of vapor that must boil off in the tank to maintain the fuel tank pressure is greatly reduced.

The fuel supply pressure control system of the present invention preferably makes use of a pressure switch, set to make or change contacts at a predetermined pressure. This is the pressure set point for the fuel supply. As long as the pressure is greater than the pressure set point, the flamer will utilize vaporous fuel. If the fuel supply pressure drops to or below the pressure set point, the contacts in the pressure switch will change, closing a vapor solenoid valve and opening a liquid solenoid valve, and liquid will be utilized by the flamer. The liquid fuel is vaporized after leaving the fuel supply tank. As the fuel travels toward the flamer torches, the pressure rises toward ambient. Boiling of the liquid fuel will result when it reaches the vaporizing portion of the torches, as the fuel attempts to reach an equilibrium state. Hence, at the torches, the fuel burned is vaporous, regardless of which solenoid valve is open at the time.

Other objects, advantages and novel features of the present invention will become apparent from the following detailed description of the invention when considered in conjunction with the accompanying drawings.

DETAILED DESCRIPTION OF THE INVENTION

Figure 1:
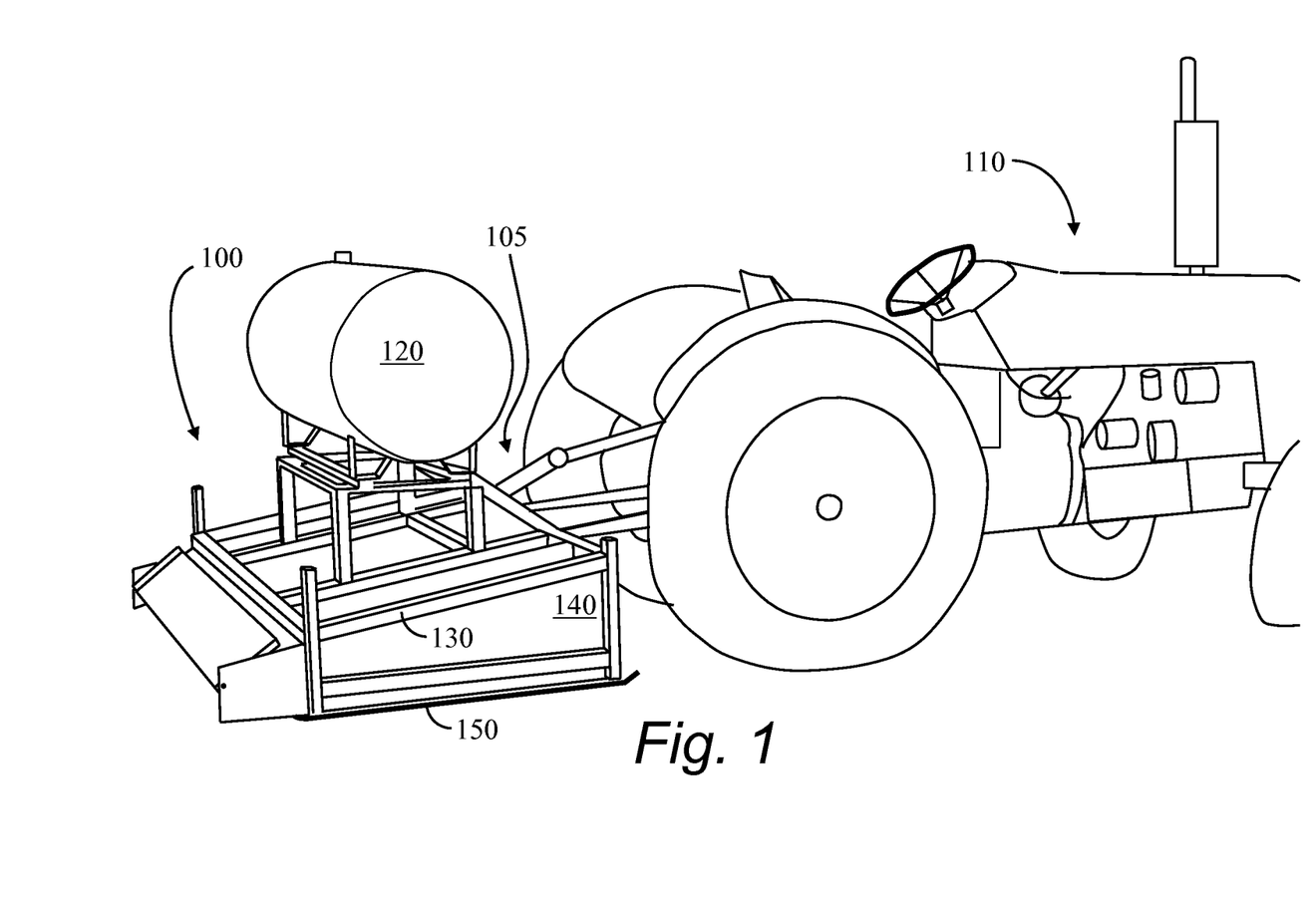
FIG. 1 is a perspective view of the tractor-mounted flamer with a fuel tank mounted thereon.
Figure 2:
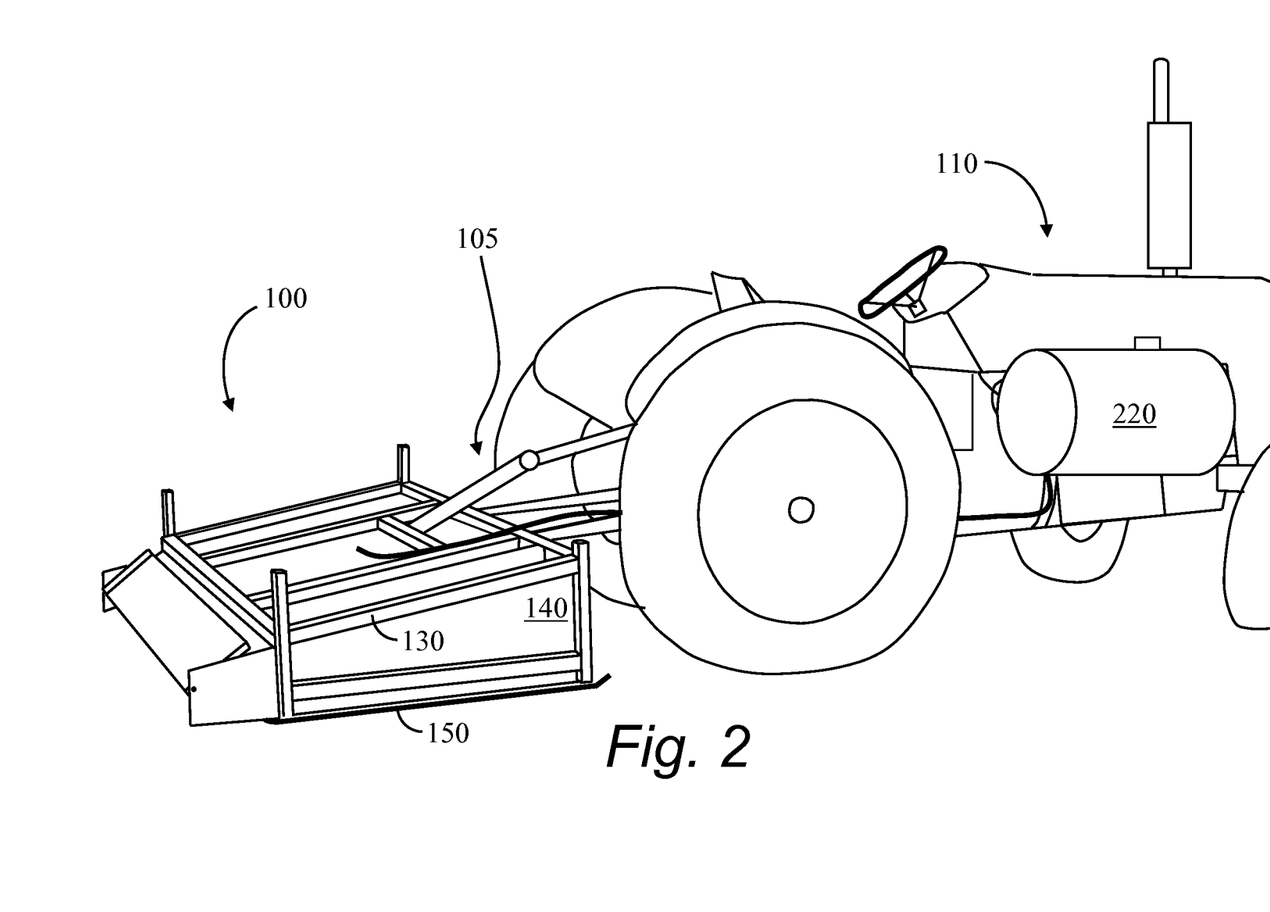
FIG. 2 is a side elevation view of the tractor-mounted flamer.
Figure 3:
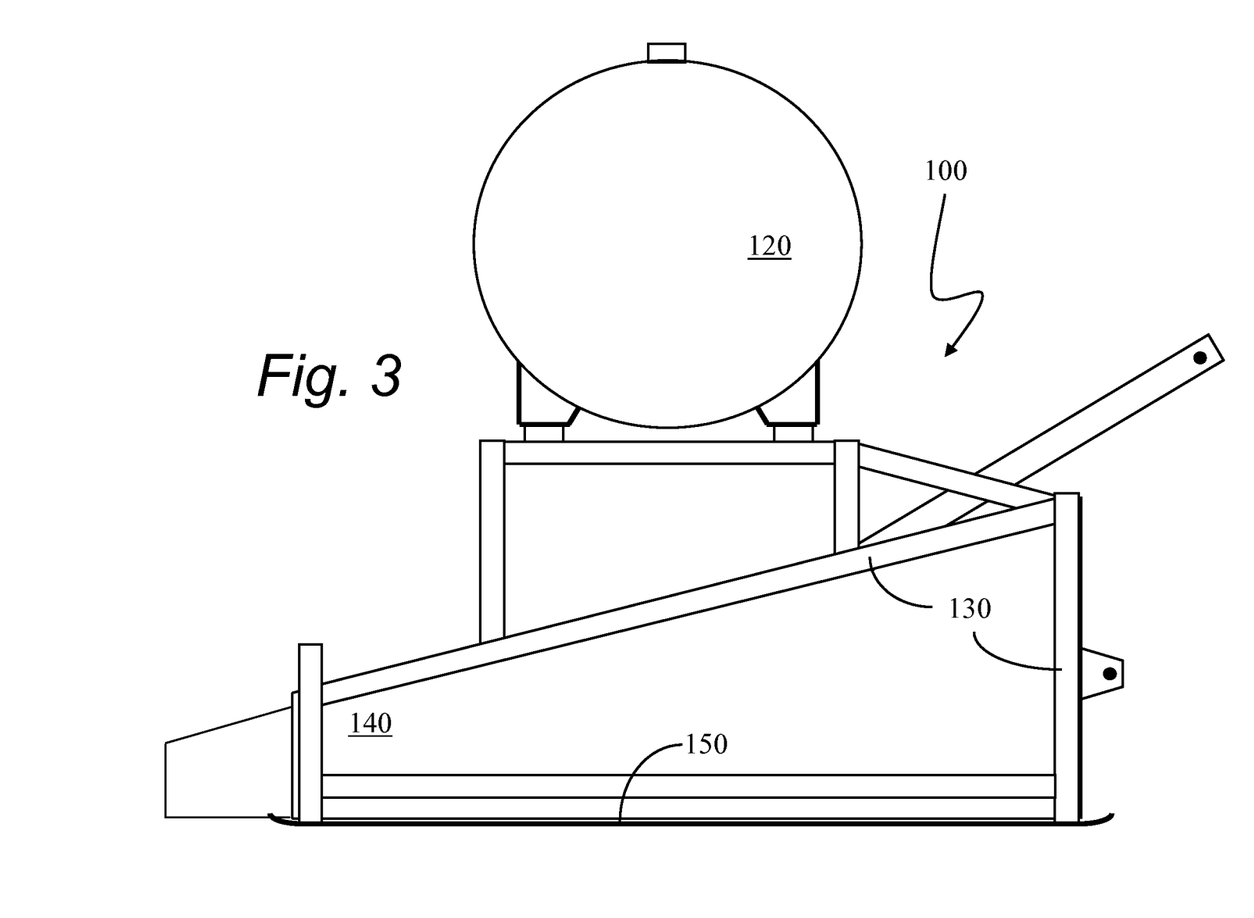
FIG. 3 is a side elevation view of the tractor-mounted flamer.
Figure 4:
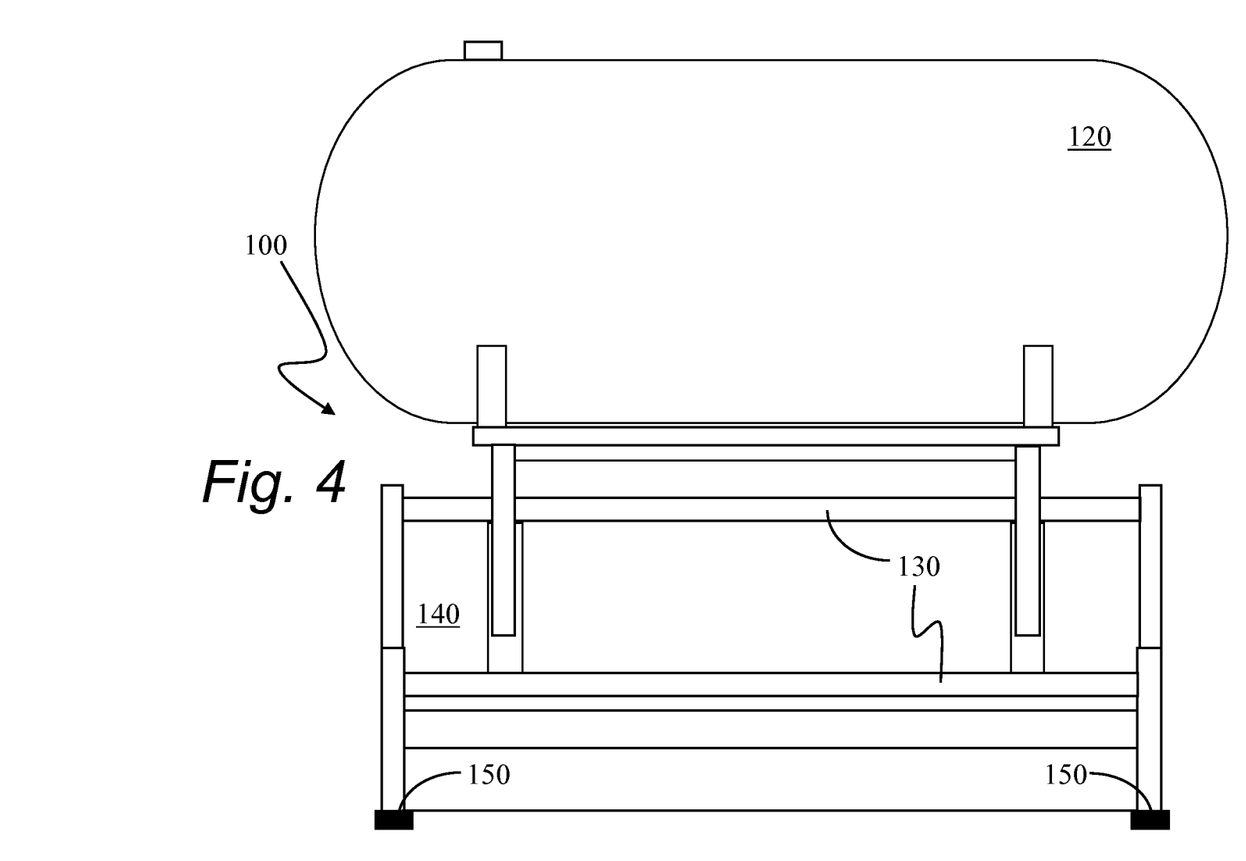
FIG. 4 is a rear elevation view of the tractor-drawn flamer.

A perspective view of one embodiment of the present invention is shown in FIGS. 1 and 2. A side view and a rear view are seen in FIGS. 3 and 4, respectively. A mobile flamer 100 is shown mounted on an implement hitch 105 of a tractor 110. Fuel may, optionally, be carried on the flamer in a fuel tank 120. In a second embodiment, the fuel may be separate from the flamer 100, for instance, carried on the tractor in a tractor-mounted fuel tank 220.

A hood for the flamer 100 comprises an external frame 130 and skin 140. Because the frame is external to the skin 140, the frame is exposed to less radiant heat transfer, reducing the problems such as oxidation and fatigue caused by high temperatures and thermal cycling. In addition, the flamer 100 can be insulated while maintaining a reflective surface inside the flamer because frame 130 members are not in the way.

The skin 140 substantially contains the high temperature gases, protecting the surroundings and concentrating the heat to the material to be sterilized.

Adjustable skids 150 are used to maintain an appropriate height above the litter or other material 700 (see FIG. 7) to be sterilized. The weight of the flamer 100 may be shifted between the tractor hitch 105 and the skids 150, as needed. The flamer 100 is picked up with the tractor hitch 105 and carried off the surface for transport, cooling, etc.

Figure 5:
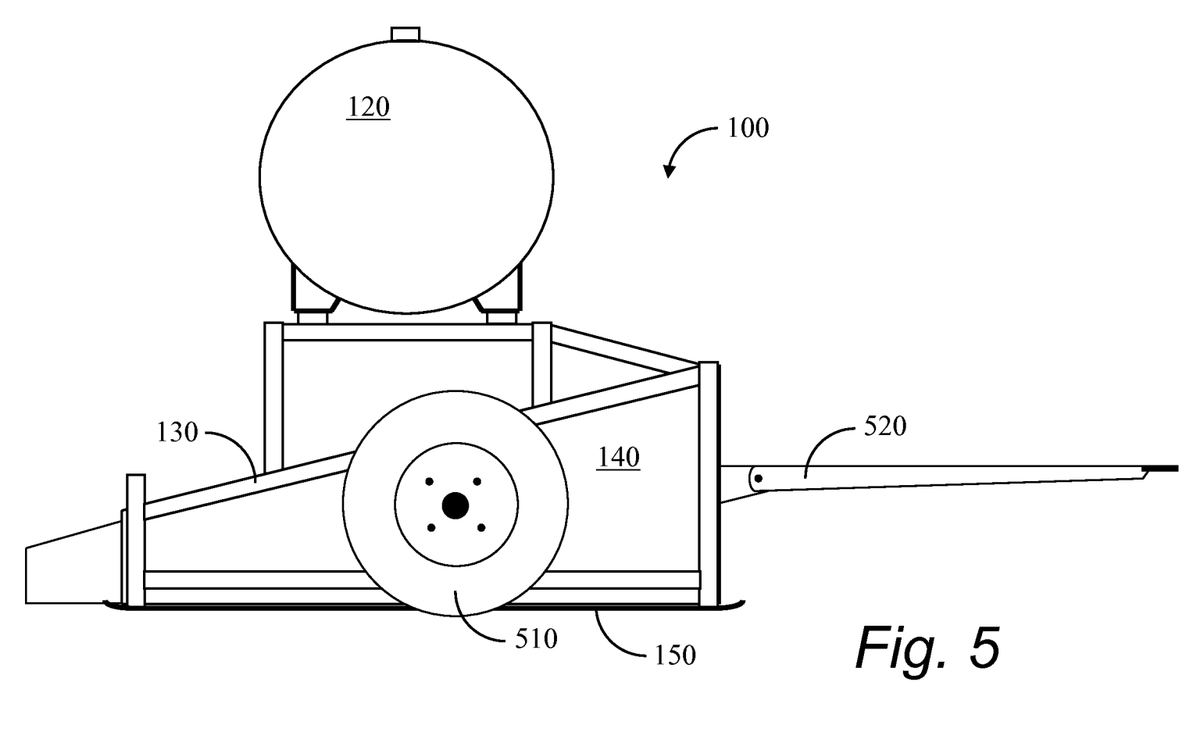
FIG. 5 is a perspective view of a wheel mounted flamer with the fuel tank mounted thereon.

An additional embodiment is shown in FIG. 5 wherein the flamer 100 is carried on wheels 510 and drawn behind the tractor 110 by its tongue 520. The wheels may be drawn up, allowing the flamer 100 to rest on its skids 150 when in use. One advantage to this embodiment is that the flamer 100 may be towed behind any of a multitude of vehicles such as a truck, four-wheeler, or tractor.

Figure 6:
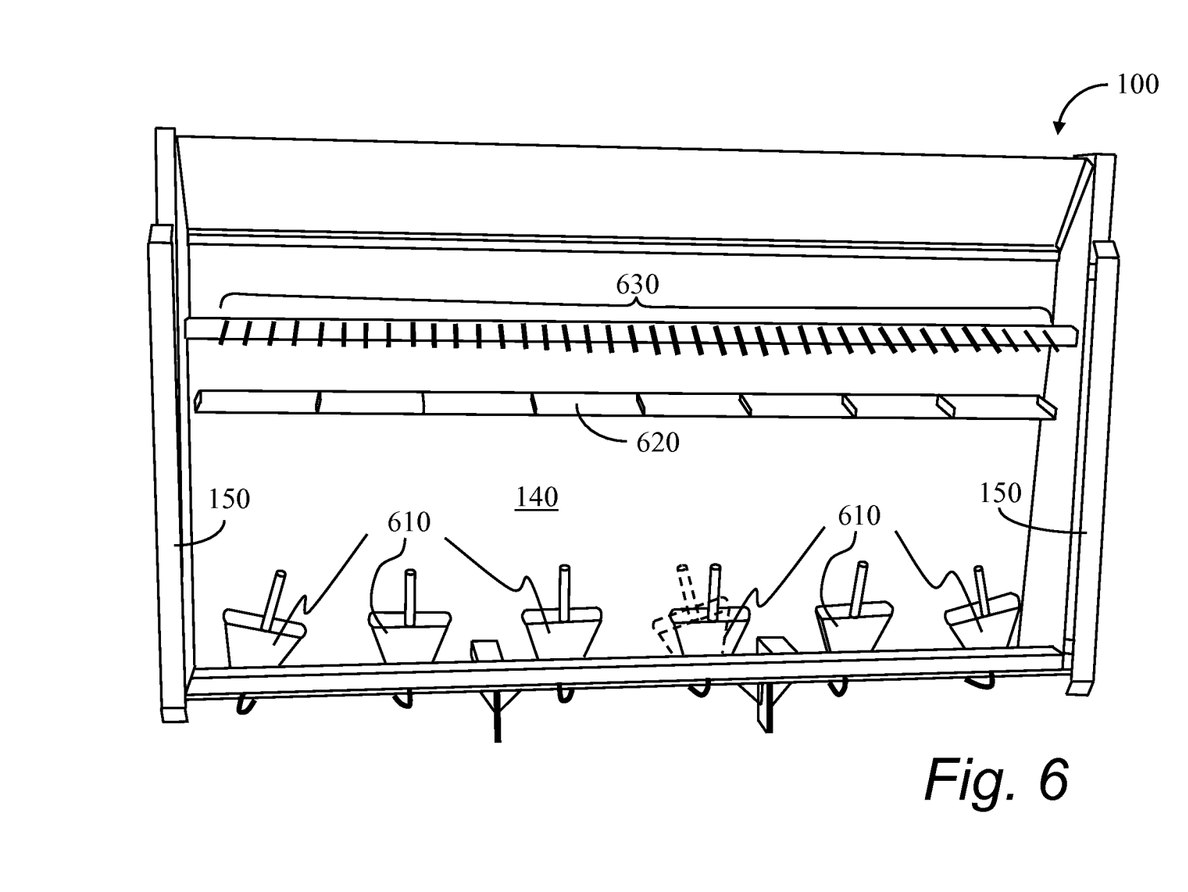
FIG. 6 is a perspective view of the underside of the tractor-mounted flamer.

The underside of the tractor-mounted flamer 100 is shown in FIG. 6. A plurality of burners 610 are arrayed across the front of the flamer 100, the angles of which are adjustable, as shown by the dashed lines. A barrier 620 may optionally be provided to assist in concentrating the heat, containing the gases, and protecting the surroundings. An additional option is shown as a set of rake teeth 630 to loosen and stir the material 700 being sterilized.

Figure 7:
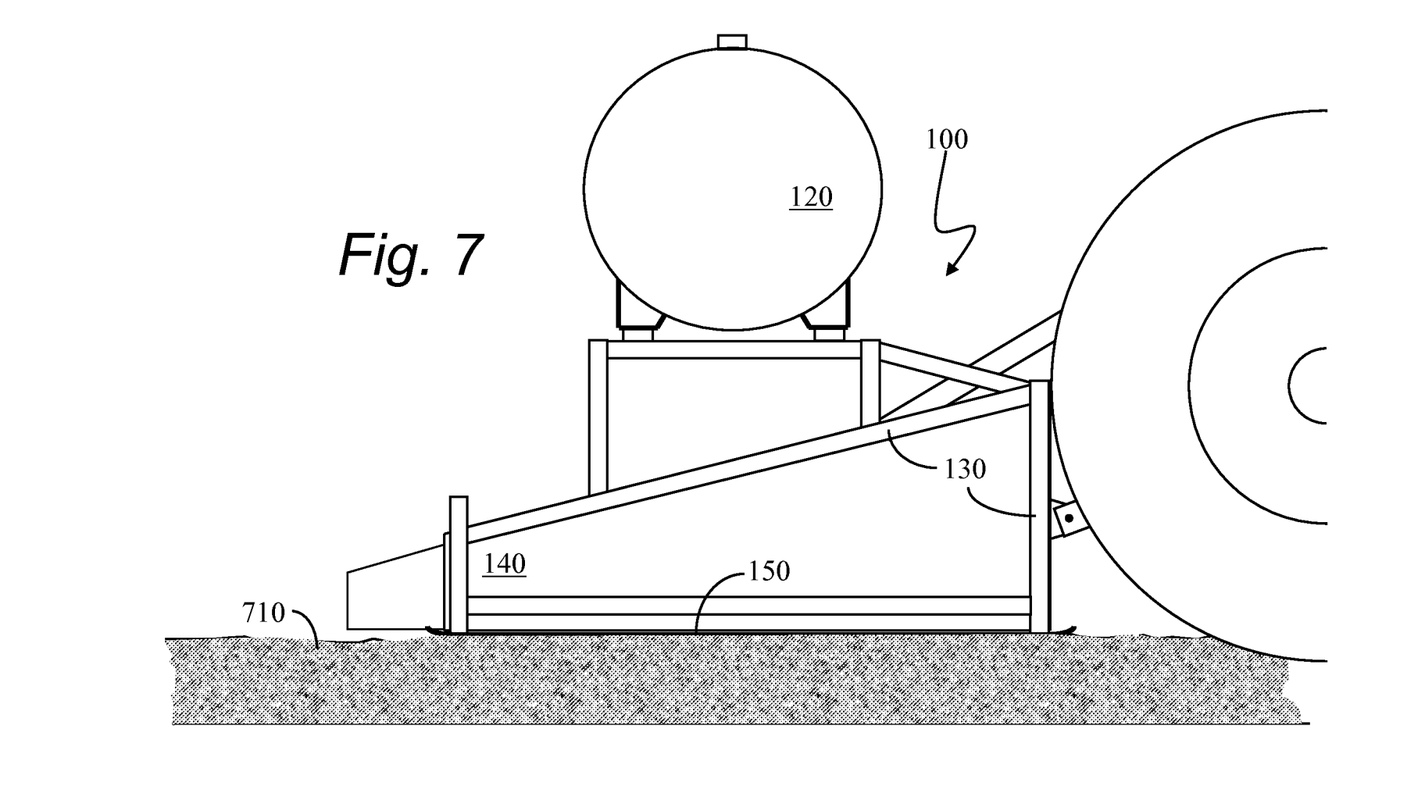
FIG. 7 is a side elevation view of the tractor-mounted flamer being used to sterilize a surface.

The mobile flamer 100 of the present invention is shown in operation in FIG. 7. The surface material 700 being sterilized may be poultry litter, other livestock manure, soil, concrete, etc.

Figure 8:
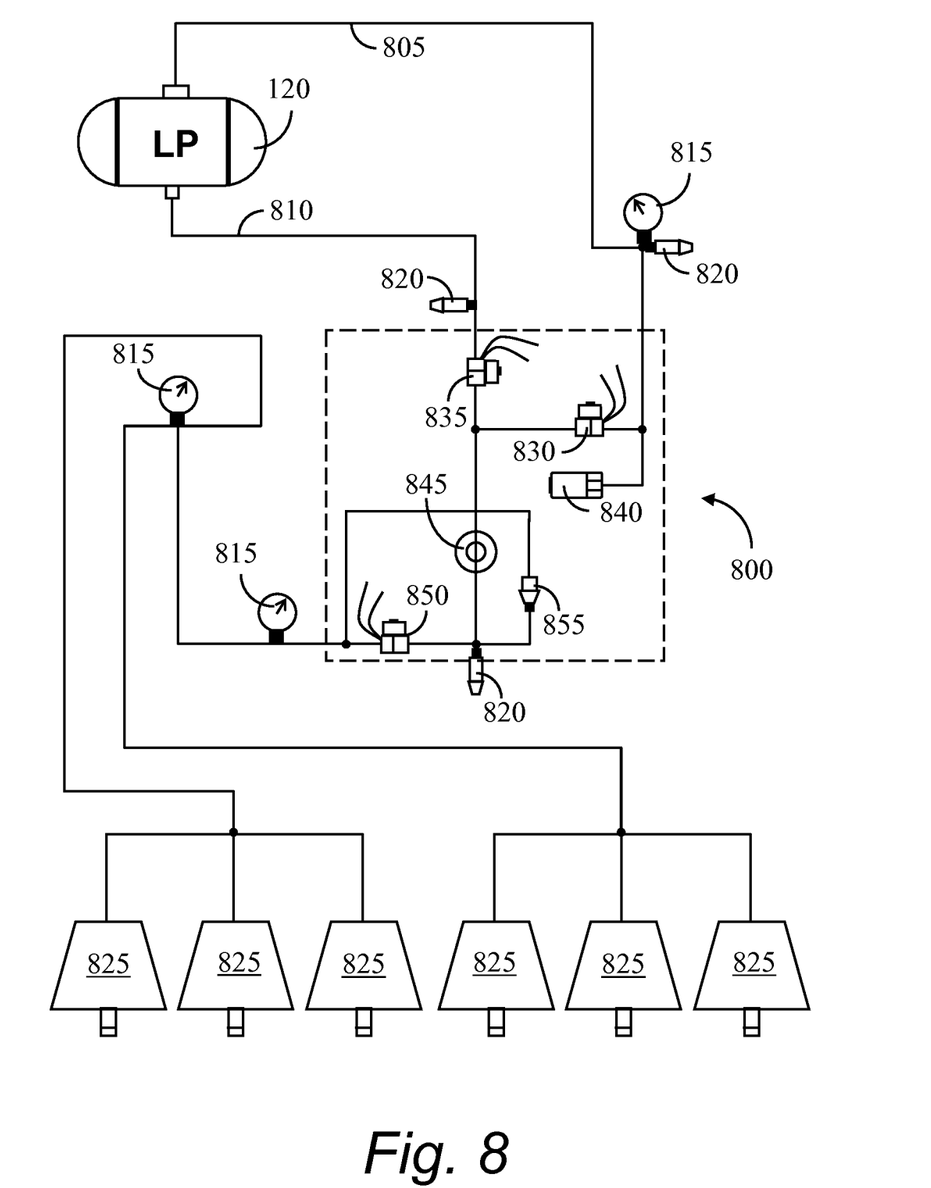
FIG. 8 is a first piping schematic for a flamer fuel supply pressure control system.

A schematic of the piping and instrumentation of the flamer fuel supply pressure control system is shown in FIG. 8. Propane is stored in the fuel supply tank 120. A vapor fuel line 805 and a liquid fuel line 810 are plumbed into the fuel supply tank 120. Note that this schematic is valid for mobile and stationary flamers.

Various pressure gages 815 are provided to give insight into the current operation of the fuel system. The pressure gages 815 may be electronic and the readings displayed at a central location. The pressure gage readings may also be incorporated into a sophisticated control system.

Pressure relief valves 820 are provided at various locations throughout the fuel system. The pressure relief valves 820 shown in FIG. 8 expel overpressured fuel into the atmosphere. Another configuration would have the overpressured fuel piped to torches 825.

The fuel supply control system 800 is shown inside the dashed lines in FIG. 8. The fuel supply control system 800 comprises a vapor line solenoid valve 830 and a liquid line solenoid valve 835. These valves are controlled by a pressure switch 840.

Figure 9:
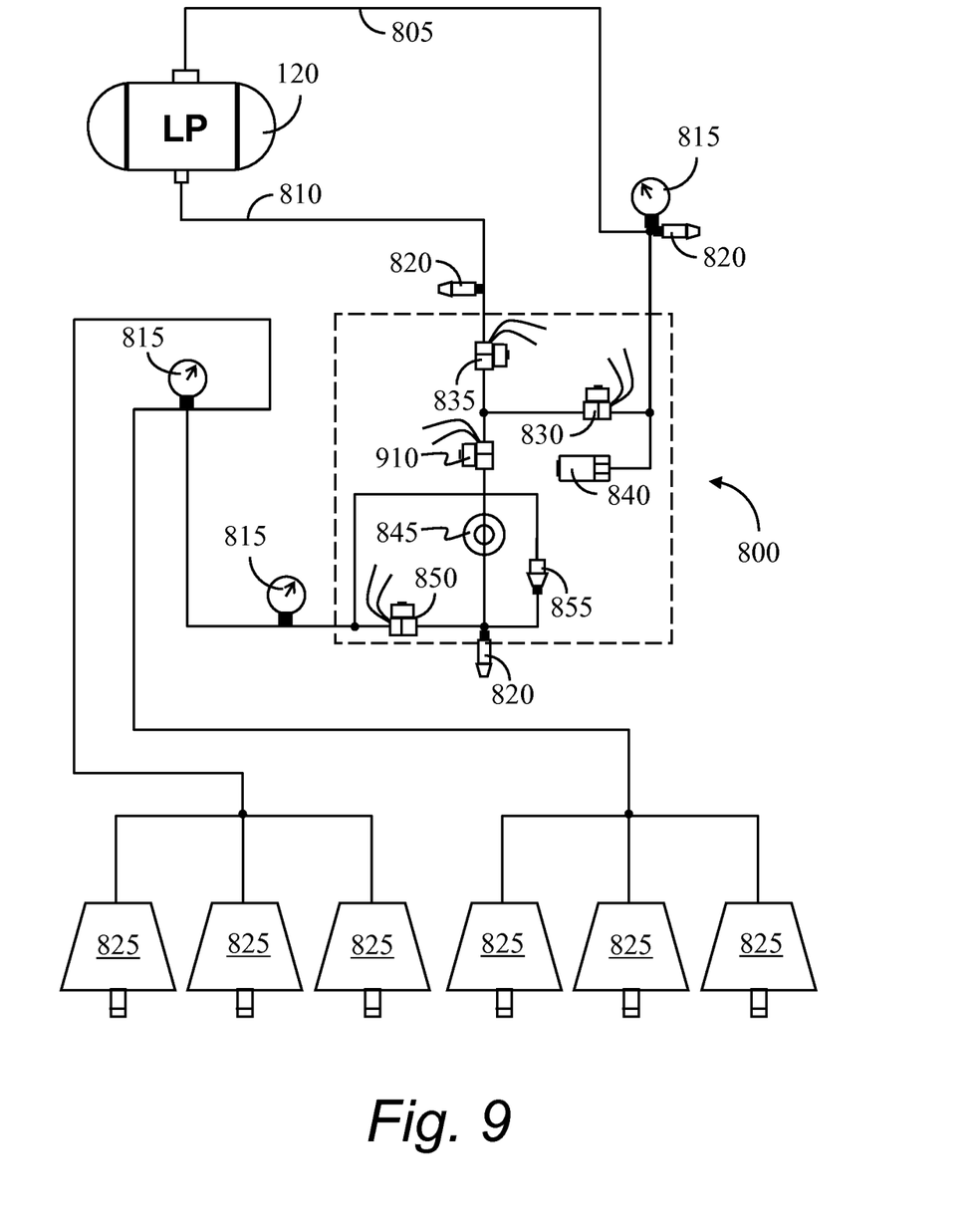
FIG. 9 is a second piping schematic for a flamer fuel supply pressure control system.

A second example of a flamer fuel system is shown in FIG. 9. In this example, a shutoff valve 910 is used to positively shut the flamer 100 down so no fuel flows.

Figure 10:
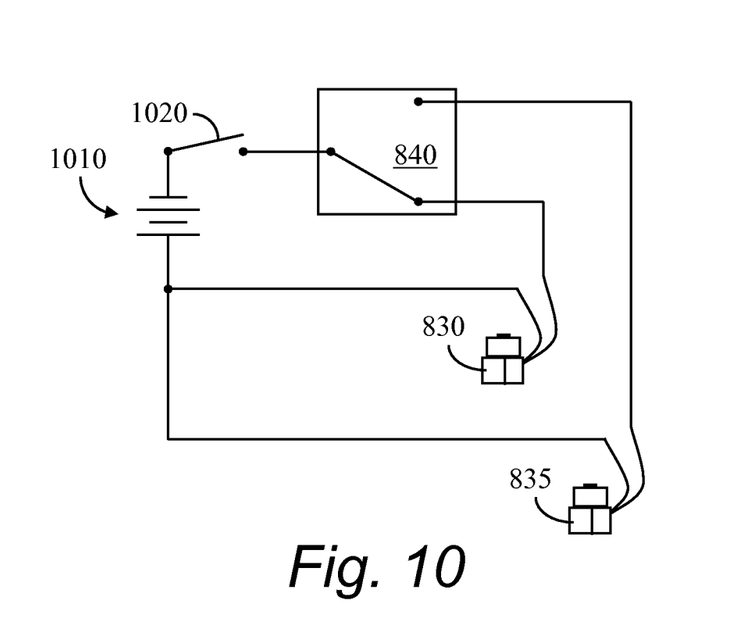
FIG. 10 is a first wiring detail for the flamer fuel supply pressure control system.
Figure 11:
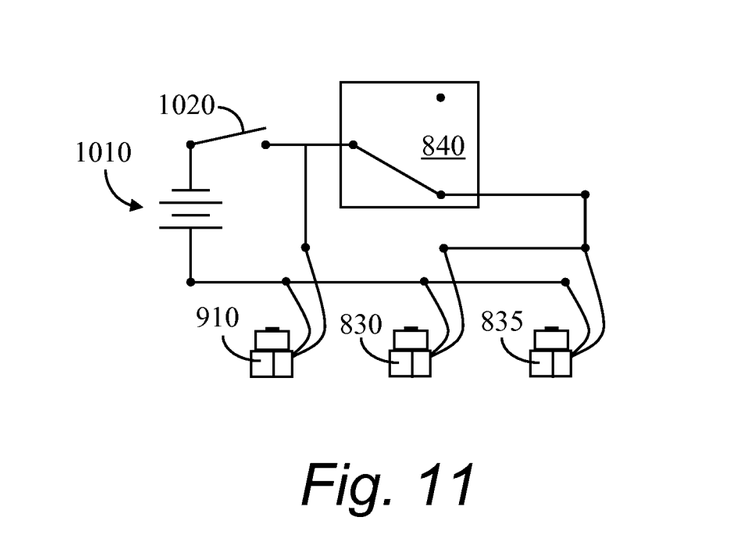
FIG. 11 is a second wiring detail for the flamer fuel supply pressure control system.

Examples of the electrical relationships between the pressure switch 840 and the solenoid valves 830, 835 are illustrated in FIGS. 10 and 11. In both these circuits, a battery 1010 is connected to the pressure switch 840 via an on/off switch 1020 which provides a shutdown of the flamer 100.

The system shown in FIG. 10 is especially suited for the piping shown in FIG. 8. In FIG. 10, the pressure switch 840 comprises a single pole double throw pressure switch. The solenoid valves 830, 835 are normally closed valves, requiring electrical excitation to open. When the fuel source pressure decreases to the preset pressure set point, the pressure switch 840 is actuated, thereby changing the pole to which the battery 1010 is connected. At high pressures, the vapor solenoid valve 830 is open while the liquid solenoid valve 835 is closed. When the pressure drops to the pressure set point and the pressure switch 840 is actuated, the liquid solenoid valve 835 opens and the vapor solenoid valve 830 closes.

The circuit shown in FIG. 11 is suited for use with the plumbing illustrated in FIG. 9. In FIG. 11, the pressure switch 840 comprises a single pole single throw pressure switch. The vapor solenoid valve 830 is a normally open valve, while the liquid solenoid valve 835 is a normally closed valve, requiring excitation to close. When the fuel source pressure decreases to the preset pressure set point, the pressure switch 840 is actuated, thereby energizing both solenoid valves 830, 835. At high pressures, when neither valve is energized, the vapor solenoid valve 830 is open while the liquid solenoid valve 835 is closed. When the pressure drops to the pressure set point and the pressure switch 840 is actuated, providing connection to the solenoid valves 830, 835, the liquid solenoid valve 835 opens and the vapor solenoid valve 830 closes.

Because the vapor solenoid valve 830 is a normally open valve and thus, fuel may flow at any time, the additional, shutoff solenoid valve 910 is needed to provide secure shutoff of the fuel. This shutoff solenoid valve 910 is a normally closed valve, hence is closes when no power is provided to it. Note that the secure shutoff solenoid valve 910 may be used with the normally closed solenoid valves 830, 835 illustrated in FIGS. 8 and 10 as well, providing redundant shutoff and the associated safety.

Other wiring configurations are possible, and the present invention is not limited to those shown in FIGS. 10 and 11.

Regardless of whether the fuel is from the liquid or vapor fractions of the tank 120, the fuel pressure is dropped through a pressure regulator 845. A shutoff solenoid valve 850 is used to turn the flamer 100 off except for a small flame, the fuel for which is provided through a needle valve 855, bypassing the shutoff solenoid valve 850. The small flame permits the torches 825 to be refired at any time.

Figure 12:
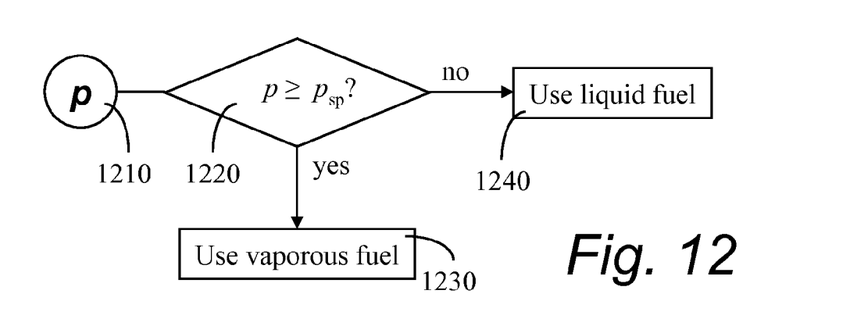
FIG. 12 is a flow diagram of the logic for the flamer fuel supply pressure control system.

In FIG. 12, a logic diagram is shown for the flamer fuel supply pressure control system 800. The fuel supply pressure 1210 is compared to a predetermined pressure set point in a comparator block 1220. This comparison is preferably carried out mechanically in the pressure switch 840. If the fuel supply pressure 1210 is greater than or equal to the pressure set point, $p_{sp}$, the vapor solenoid valve 830 is open and vaporous fuel is used 1230 by the flamer 100. If the fuel supply pressure 1210 is less than the pressure set point, $p_{sp}$, the liquid solenoid valve 835 is open and liquid fuel is used 1240 by the flamer 100.

Note that appropriate hysteresis is required in the pressure switch 840 to avoid rapid switching between liquid and vaporous fuel.

Figure 13:
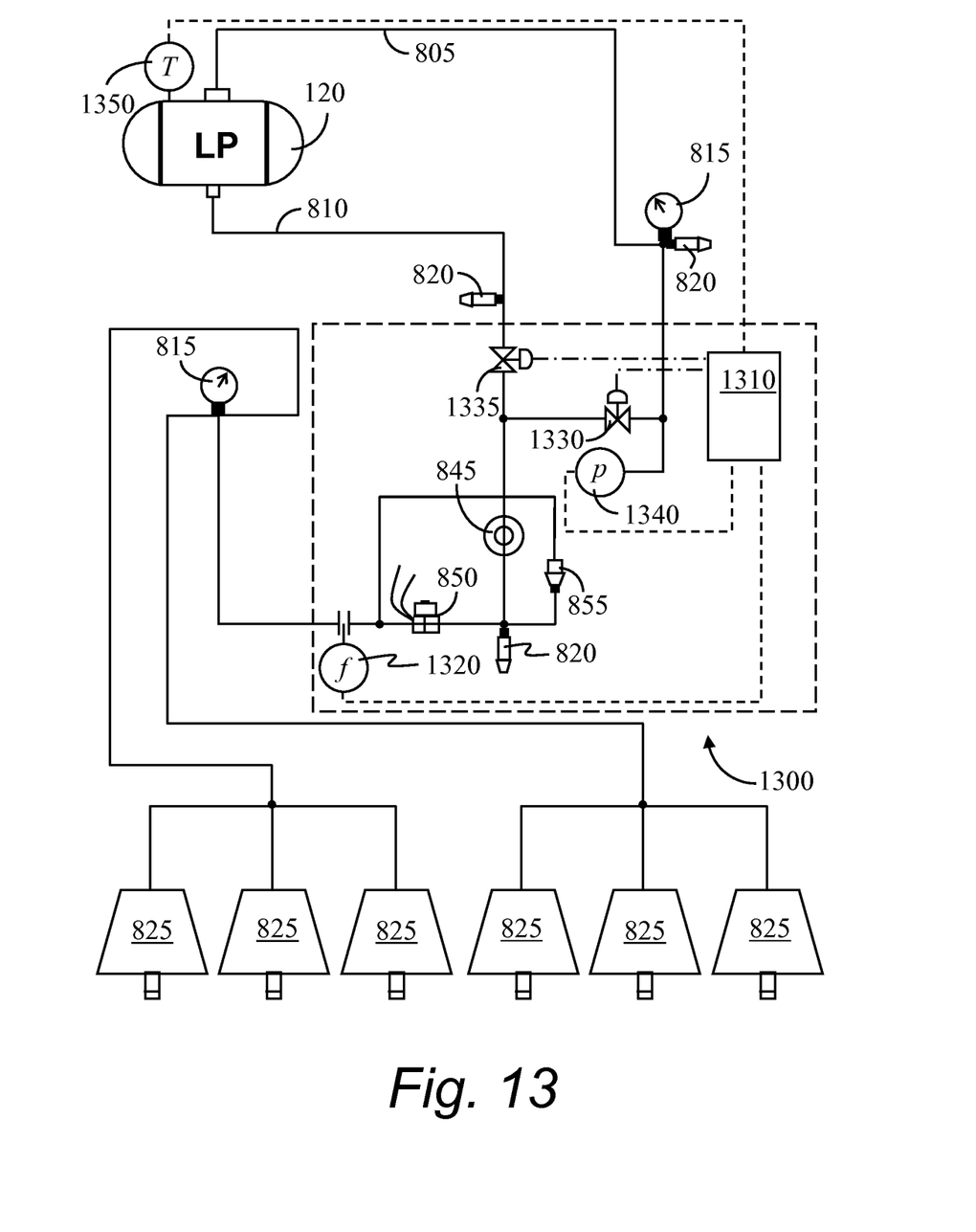
FIG. 13 is a third piping schematic for a flamer fuel supply pressure control system.
Figure 14:
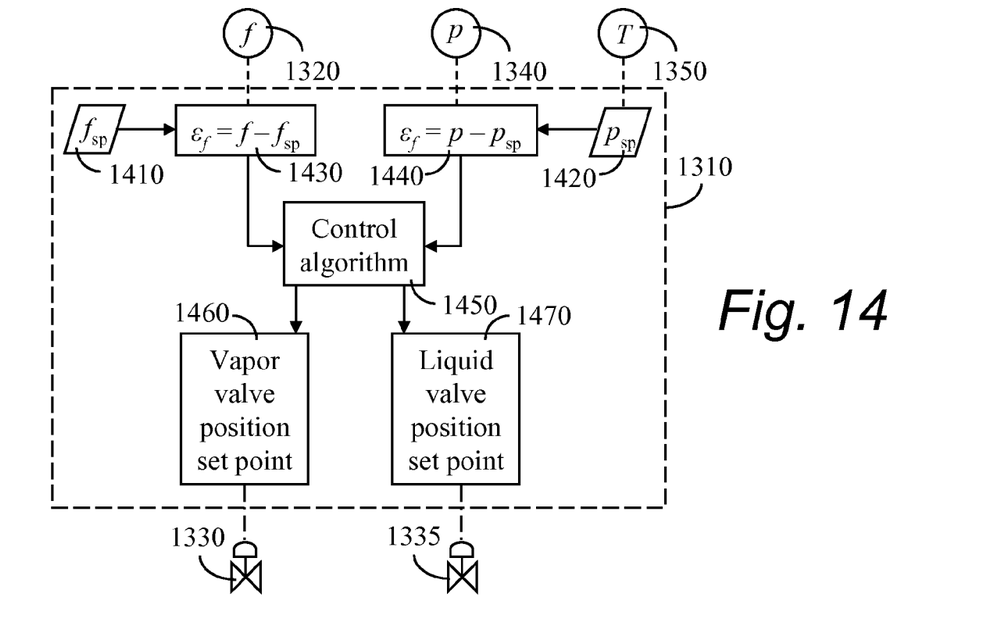
FIG. 14 is a detail of a flamer fuel supply pressure controller.

A second embodiment of the present invention includes the flamer fuel pressure control system 1300 depicted in FIGS. 13 and 14. In this embodiment, an electronic controller 1310, either analog or digital, accepts a flow signal from a flow transmitter 1320 and a pressure signal from a pressure transmitter 1340. Measurement and/or calculation of these values are well known to those of ordinary skill in the art. The electronic controller 1310 uses these signals to calculate an output for each of two control valves 1330, 1335. The flow of vapor is continuously controlled by the vapor control valve 1330, while the flow of liquid is continuously controlled by the liquid control valve 1335.

The electronic controller 1310 is detailed in FIG. 14. The flow and pressure signals, from the associated transmitters 1320, 1340 are shown input into the electronic controller 1310. A flow set point 1410 is also available to the electronic controller 1310, adjustable by an operator. The pressure set point 1420 may be predetermined by an operator, or it may be calculated as a function of a tank temperature signal from a temperature sensor 1350, also shown in FIG. 13. In the usual fashion, as understood by those of ordinary skill in the art, errors, $\epsilon_f$, and $\epsilon_p$, for each of the controlled variables, $f$ and $p$, are calculated in the respective calculation blocks 1430, 1440. These are utilized in a control algorithm or algorithms 1450 such as a pair of Proportional Integral Differential (PID) loops with decoupling between the loops, or a multivariable algorithm such as a matrix control algorithm. These algorithms, as well as others, are well known in the art. The present invention is not limited to a particular automatic control algorithm 1450.

Outputs of the control algorithm 1450 include valve position set points 1460, 1470 for each of the two control valves 1330, 1335.

The above embodiments are the preferred embodiments, but this invention is not limited thereto. It is, therefore, apparent that many modifications and variations of the present invention are possible in light of the above teachings. It is, therefore, to be understood that within the scope of the appended claims, the invention may be practiced otherwise than as specifically described.

I claim:

1. An apparatus for providing pressure control for a flamer fuel system using a fuel comprising a saturated liquid-vapor mixture, the apparatus comprising:
   (a) a vapor control valve installed in a vapor fuel line through which saturated vapor fuel is extracted from the saturated liquid-vapor mixture;
   (b) a liquid control valve installed in a liquid fuel line through which saturated liquid fuel is extracted from the saturated liquid-vapor mixture; and
   (c) a pressure switch having a predetermined pressure set point to selectively switch between the vapor control valve and the liquid control valve based on a flamer fuel system pressure.

2. The apparatus of claim 1 wherein the vapor control valve and the liquid control valve comprise solenoid actuated control valves.

3. The apparatus of claim 1 including wiring wherein the pressure switch is wired to the vapor control valve and the liquid control valve such that the vapor control valve is open and the liquid control valve is closed when the flamer fuel system pressure is greater than a predetermined pressure set point and the vapor control valve is closed and the liquid control valve is open when the flamer fuel system pressure is less than the predetermined pressure set point.

* * * * *